US009475686B2

(12) United States Patent
Tuohey et al.

(10) Patent No.: US 9,475,686 B2
(45) Date of Patent: Oct. 25, 2016

(54) DISPOSABLE VALVE AND FLEXIBLE CONTAINERS FOR PRESSURIZED BIOREACTORS

(71) Applicant: GE HEALTHCARE BIO-SCIENCES CORP., Piscataway, NJ (US)

(72) Inventors: Colin R. Tuohey, Medway, MA (US); Thomas Erdenberger, Arlington, MA (US); Richard L. Damren, Marlborough, MA (US); Kenneth Clapp, Marlborough, MA (US); Parrish M. Galliher, Littleton, MA (US); Jonathan Kenney, Lakeville, MA (US)

(73) Assignee: GE HEALTHCARE BIO-SCIENCES CORP., Piscataway, NJ (US)

( * ) Notice: Subject to any disclaimer, the term of this patent is extended or adjusted under 35 U.S.C. 154(b) by 180 days.

(21) Appl. No.: 14/383,328

(22) PCT Filed: Mar. 7, 2013

(86) PCT No.: PCT/US2013/029635
§ 371 (c)(1),
(2) Date: Sep. 5, 2014

(87) PCT Pub. No.: WO2013/134515
PCT Pub. Date: Sep. 12, 2013

(65) Prior Publication Data
US 2015/0053307 A1 Feb. 26, 2015

Related U.S. Application Data

(60) Provisional application No. 61/607,767, filed on Mar. 7, 2012, provisional application No. 61/608,438, filed on Mar. 8, 2012.

(51) Int. Cl.
*B67D 7/02* (2010.01)
*C12M 1/00* (2006.01)
(Continued)

(52) U.S. Cl.
CPC .............. *B67D 7/0294* (2013.01); *B67D 7/36* (2013.01); *B67D 7/84* (2013.01); *C12M 23/14* (2013.01);
(Continued)

(58) Field of Classification Search
CPC ........ B67D 7/02; B67D 7/0294; B67D 7/36; B67D 7/54; F16K 7/10; F16K 1/04; F16K 1/20; F16K 1/24; F16K 31/22; F16K 31/508; F16K 31/126
USPC .......................... 141/287; 137/852; 251/175
See application file for complete search history.

(56) References Cited

U.S. PATENT DOCUMENTS 4,155,373 A * 5/1979 DiGiovanni .............. F16K 7/10
137/15.15
4,742,956 A 5/1988 Zelczer
(Continued)

FOREIGN PATENT DOCUMENTS

CA 2073844 A1 1/1994
CN 101387286 A 3/2009
(Continued)

OTHER PUBLICATIONS

Supplementary European Search Report received for European Patent Application No. EP13757342.4, dated Sep. 24, 2015, 9 pages.
(Continued)

*Primary Examiner* — Timothy L Maust
(74) *Attorney, Agent, or Firm* — Grogan, Tuccillo & Vanderleeden, LLP

(57) ABSTRACT

Disclosed herein are embodiments of a valve assembly for preventing dead leg spaces in a container or tubing, the embodiments including a three-way valve system for controlling back-pressure in a fluid generating device, such as a single-use high pressure bioreactor. Also disclosed is a pressurized reactor system for bioprocessing, comprising a single-use container including a flexible wall or a semi-rigid wall.

5 Claims, 13 Drawing Sheets

(51) Int. Cl.
*F16K 31/44* (2006.01)
*F16K 1/04* (2006.01)
*F16K 1/20* (2006.01)
*F16K 1/24* (2006.01)
*F16K 7/10* (2006.01)
*B67D 7/36* (2010.01)
*B67D 7/84* (2010.01)
*F16K 31/126* (2006.01)
*F16K 31/22* (2006.01)
*F16K 31/50* (2006.01)
*B01F 13/08* (2006.01)
*B01F 15/00* (2006.01)

(52) U.S. Cl.
CPC ............. *C12M 23/28* (2013.01); *C12M 29/14* (2013.01); *F16K 1/04* (2013.01); *F16K 1/20* (2013.01); *F16K 1/24* (2013.01); *F16K 7/10* (2013.01); *F16K 31/126* (2013.01); *F16K 31/22* (2013.01); *F16K 31/44* (2013.01); *F16K 31/508* (2013.01); *B01F 13/08* (2013.01); *B01F 15/0085* (2013.01)

(56) References Cited

U.S. PATENT DOCUMENTS

| | | | | |
|---|---|---|---|---|
| 4,787,408 A | * | 11/1988 | Twerdochlib | ............. F16K 7/10 137/14 |
| 5,065,980 A | | 11/1991 | Pedersen | |
| 5,333,653 A | * | 8/1994 | Rzesutock | ............... B67D 7/04 141/1 |
| 5,786,209 A | | 7/1998 | Newberg | |
| 5,988,422 A | | 11/1999 | Vallot | |
| 8,544,894 B1 | * | 10/2013 | Borba | ...................... E03F 1/008 141/287 |
| 2003/0019539 A1 | | 1/2003 | Hornwood | |
| 2011/0198286 A1 | | 8/2011 | Niazi | |

FOREIGN PATENT DOCUMENTS

| | | |
|---|---|---|
| EP | 0069807 A1 | 1/1983 |
| WO | 03/093706 A1 | 11/2003 |
| WO | 2009/012563 A1 | 1/2009 |
| WO | 2010/112067 A1 | 10/2010 |
| WO | WO 2011/041508 | 4/2011 |

OTHER PUBLICATIONS

State Intellectual Property Office, P.R. China, Office Action for Patent Application No. 201380012648.4, mailed on Oct. 9, 2015, 11 pages.

State Intellectual Property Office of People's Republic China Search Report for Application No. 201380012648.4 mailed Sep. 24, 2015, 4 pages.

* cited by examiner

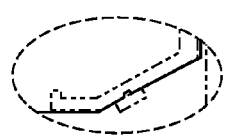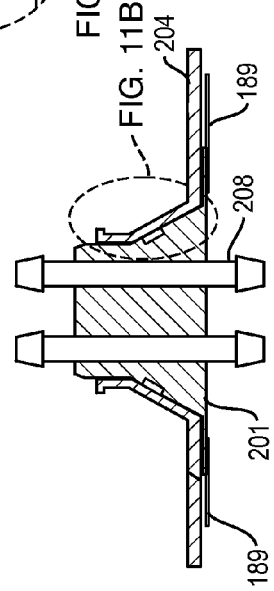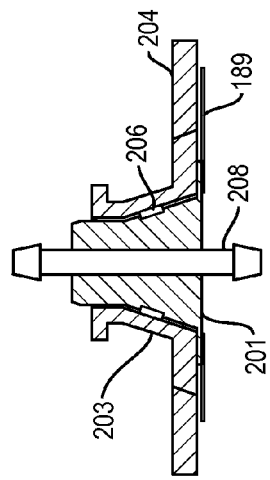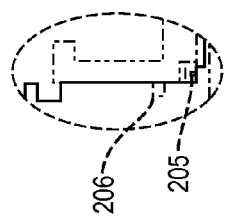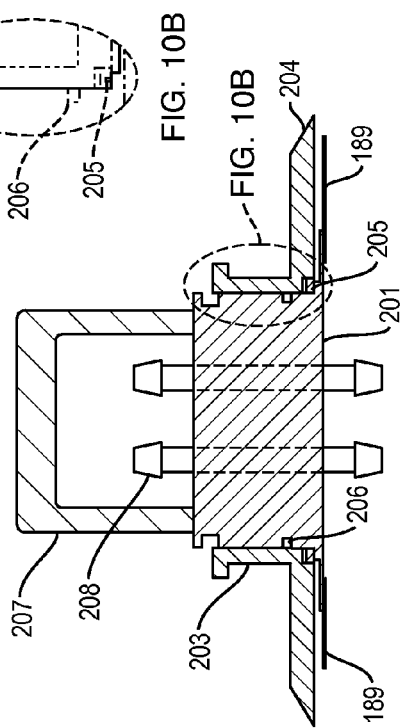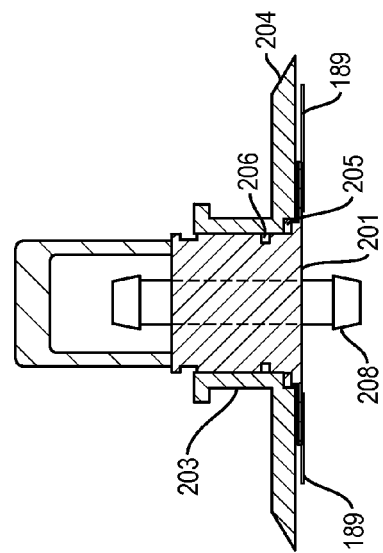

DISPOSABLE VALVE AND FLEXIBLE CONTAINERS FOR PRESSURIZED BIOREACTORS

CROSS-REFERENCE TO RELATED APPLICATIONS

This application is a filing under 35 U.S.C. 371 of international application number PCT/US2013/029635, filed Mar. 7, 2013, published on Sep. 12, 2013 as WO 2013/134515, which claims priority to U.S. provisional patent application Nos. 61/607,767 filed Mar. 7, 2012 and 61/608,438 filed Mar. 8, 2012.

BACKGROUND

In the biopharmaceutical industry, increasingly, single-use or disposable containers or flexible bags are used. Such containers can be flexible or collapsible plastic bags that are supported by an outer rigid structure such as a stainless steel shell, the support structure also referred to herein as a "vessel." Use of sterilized disposable bags eliminates the time-consuming step of cleaning the steel bioreactor and reduces the chance of contamination. Combining the single-use or disposable bags with a magnetically coupled agitator system establishes a sterile environment that is especially important for biopharmaceutical manufacturing.

Currently available single-use bioreactors utilize hose barb or similar fittings that are welded to the bag film as entry and exit points for conveyance of fluid. The fitting for a drain line on a bioreactor is typically located at the bottom of the bag. The drain line fitting generally has a tubular portion that is commonly described as a "dead-leg," because it is a one-way fluid flow system. Media flows into the dead-leg portion of the fitting, where media, cells and other fluid components can settle and remain isolated from the bulk bioreactor environment. When cells collect in this portion of the fitting, they are generally deprived of nutrients, die, and release toxic compounds that can be detrimental to the growth and production of cells in the bulk culture. At present there is no effective means for preventing or completely eliminating this isolated volume of fluid and cells in a dead-leg portion of a drain fitting.

Currently available valves that are employed on single-use bioreactors include a non-invasive pinch valve, comprising flexible plastic or rubber tubing placed inside a valve body and a clamp or other means for pinching the tubing in order to close the channel in the tubing. Another type of valve includes a flexible tubing placed inside a valve body, and a plunger arranged to be forced down through the channel in the tubing to restrict flow. There are disadvantages associated with these currently available valves. For example, the rubber or plastic tubing over time becomes fatigued from constant compression or from curing of the polymer material, leading to breakage and/or particle generation. Either of these can be detrimental to bioprocessing by either contaminating the culture or by generating particles that will flow into the bulk fluid. Another type of valve is an in-line fitting to which tubing is connected, the valve including a ball with a hole therethrough, such that in one position the flow path is open, and if rotated 90 degrees the flow path is closed.

Another on-going problem related to the use of single-use flexible or semi-rigid bioreactor bags is that many chemical, biological or pharmaceutical manufacturing processes are preferably conducted at pressures significantly above or below atmospheric pressure. Such processes have typically required rigid vessels, such as stainless steel bioreactors, that can withstand high positive or negative pressures. Flexible wall disposable single-use manufacturing systems, on the other hand, typically have limited capability of withstanding relatively high pressures. In addition, installing flexible containers or wall liners in pressurizable support structures can lead to difficulties in loading and unloading the disposable component from the system. The pressurizable support structure requires openings large enough to insert and remove the disposable reactant container easily. Consequently, lids, seals and fasteners must be designed to cover such openings so that they are strong enough to withstand the forces involved. As the size of the vessels increases, the ergonomics of bag unloading and loading worsen and the heavier vessel hardware becomes more complicated to operate.

Thus there is a currently unmet need for both non-dead leg valves for use in single-use, flexible bioreactor containers and for high performance flexible containers for use in pressurized biological manufacturing processes.

BRIEF SUMMARY OF THE DISCLOSURE

In accordance with the present invention there is provided a valve assembly for preventing dead leg spaces in a container or tubing, the valve assembly comprising: a bulkhead fitting for attaching the valve assembly to a flexible or semi-rigid wall of the container or tubing, the bulkhead fitting comprising an annular flange for mounting on one side of the flexible or semi-rigid wall of the container or tubing such that an opening in the center of the annular flange is in communication with an aperture in the flexible or semi-rigid wall of the container or tubing; a hollow housing attached to or integral with the annular flange of the bulkhead fitting, the hollow housing comprising: a liquid inlet communicating with the opening in the center of the annular flange and configured for receiving a liquid from the container or tubing; a liquid outlet; a gas port configured to be attached to a gas passageway and valve, wherein the valve is configured to selectively allow gas flow into the gas port or out of the gas port; and an inflatable and deflatable bellows or balloon fluidically connected to the gas port, and configured in a manner to inflate when gas flows into the gas port and into the inflatable bellows or balloon, thereby blocking the opening in the center of the annular flange and the aperture in the flexible or semi-rigid wall of the container or tubing, and to deflate when a vacuum is applied to the gas port, causing gas to flow out of the gas port and out of the bellows or balloon, thereby allowing liquid to flow out of the container or tubing, through the aperture in the flexible or semi-rigid wall of the container or tubing, through the hollow housing, and out of the liquid outlet of the hollow housing, the valve assembly thereby capable of preventing dead leg spaces in the container or tubing.

Another embodiment of the invention is a valve assembly for preventing dead leg spaces in a container or tubing, the valve assembly comprising:
a first component comprising a bulkhead fitting for attaching the valve assembly to the inside of a flexible or semi-rigid wall of the container or tubing, the bulkhead fitting comprising an annular flange for mounting on the inside of the flexible or semi-rigid wall of the container or tubing such that an opening in the center of the annular flange is in communication with an aperture in the flexible or semi-rigid wall of the container or tubing; a hollow housing attached to or integral with the annular flange of the bulkhead fitting, the hollow housing comprising: a liquid inlet communicating with the opening in the center of the annular flange and configured for receiving a liquid from the container or tubing; a liquid outlet; and a second component comprising a hollow tubing having a first end mounted at the flexible or semi-rigid wall of the container or tubing, the first end of the hollow tubing communicating with a gas port in the flexible or semi-rigid wall of the container or tubing, the second end of the hollow tubing having an inflatable and deflatable hollow member in fluidic communication with the hollow tubing and sized to seal the opening in the center of the annular flange; the inflatable and deflatable hollow member comprising a hinged portion attached to the annular flange and supporting the hollow member for reciprocating movement between a lower position where the hollow member is compressed by a hydrostatic pressure of fluid in the container or tubing and seals the opening in the center of the annular flange, preventing fluid from entering the hollow housing and an upper position spaced from the lower position, the upper position providing an opening for fluid flow through the opening in the center of the annular flange; and a means coupled to the second component and extending outside the container or tubing for selectively moving the hollow member between the upper and the lower positions.

In one embodiment of the disclosed valve assembly, the means for selectively moving the hollow member between the upper and the lower positions comprises a gas flow through the gas port, into the hollow tubing, and into the hollow member, wherein the hollow member is inflated with sufficient gas pressure to move the hollow member from the lower position to the upper position.

Yet another embodiment of the invention is a three-way valve assembly for controlling back-pressure in a fluid generating device, the three-way valve assembly comprising: a main valve body portion adapted at one end to engage an inlet for exhaust fluid from the fluid generating device, the main valve body portion defining a central axis; a bellows or valve stem having a first end and a second end, comprising a solid plunger at the first end and disposed axially within the main valve body portion, the bellows or valve stem supported for reciprocating axial movement between a first position wherein the solid plunger closes the inlet for exhaust fluid from the fluid generating device and a second position wherein the solid plunger opens the inlet for exhaust fluid from the fluid generating device; and a two-way valve coupled to the second end of the bellows or valve stem, the two-way valve configured to selectively control a gas inlet for inflating the bellows and a gas outlet for deflating the bellows.

Also disclosed is a valve assembly for preventing dead leg spaces in a container or tubing, the valve assembly comprising: a bulkhead fitting for attaching the valve assembly to a flexible or semi-rigid wall of the container or tubing, the bulkhead fitting comprising an annular flange for mounting on one side of the flexible or semi-rigid wall of the container or tubing such that an opening in the center of the annular flange is in communication with an aperture in the flexible or semi-rigid wall of the container or tubing; a hollow housing attached to or integral with the annular flange of the bulkhead fitting, the hollow housing comprising: a liquid inlet communicating with the opening in the center of the annular flange and configured for receiving a liquid from the container or tubing; a liquid outlet; a solid plunger disposed axially within the hollow housing and supported for reciprocating axial movement between a first position wherein the solid plunger closes the opening in the center of the annular flange and a second position wherein the solid plunger is raised above the level of the annular flange, allowing the liquid from the container or tubing to flow through a portion of the opening in the center of the annular flange.

The invention also relates to a pressurized reactor system for bioprocessing, the pressurized reactor system comprising: a single-use container comprising a flexible wall or a semi-rigid wall including at least one of a pressure fitting and a reinforcement; and a webbing or netting surrounding at least a portion of the flexible or semi-rigid wall.

BRIEF DESCRIPTION OF THE DRAWINGS

Embodiments of the invention are further described hereinafter with reference to the accompanying drawings, in which:

FIG. 10 is a schematic, cross-sectional view of one embodiment of a pressure fitting according to the invention.

FIG. 11 is a schematic, cross-sectional view of another embodiment of a pressure fitting according to the invention.

FIG. 12 is a schematic, cross-sectional view of another embodiment of a pressure fitting according to the invention.

FIG. 13 is a schematic, cross-sectional view of yet another embodiment of a pressure fitting according to the invention.

DETAILED DESCRIPTION

A description of preferred embodiments of the invention follows. It will be understood that the particular embodiments of the invention are shown by way of illustration and not as limitations of the invention. At the outset, the invention is described in its broadest overall aspects, with a more detailed description following. The features and other details of the compositions and methods of the invention will be further pointed out in the claims.

Figure 1A:
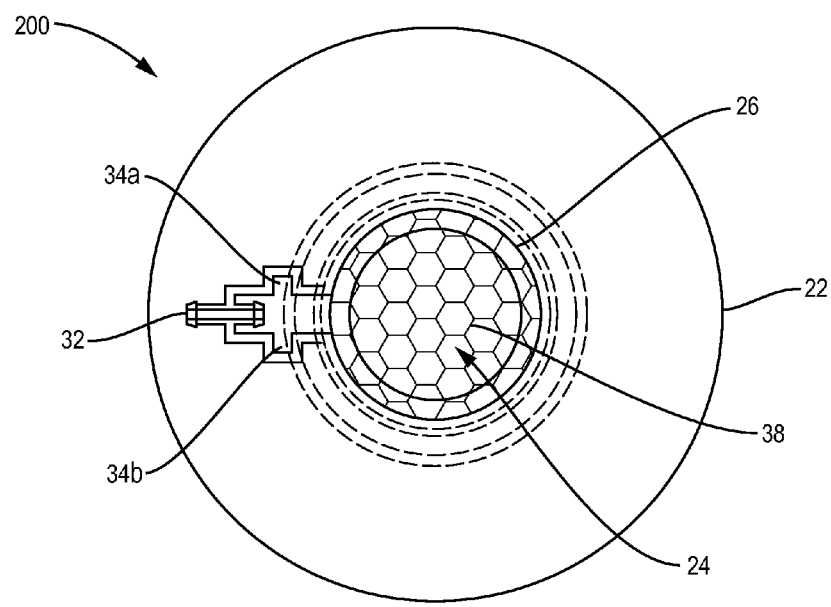
FIG. 1A is a top plan view of a single-use flush mount, balloon seal valve according to an embodiment of the invention.

We have now discovered a valve assembly for preventing dead leg spaces in a flexible or semi-rigid wall of a container or tubing. One embodiment of the invention is a bellows or balloon valve shown in FIG. 1A and FIG. 1B. FIG. 1A is a top plan view 200 of a single-use deflated bellows style, single-use valve assembly for preventing dead leg spaces in a container or tubing.

A valve according to an embodiment of the invention may be referred to herein as a "non-dead leg valve," or a "zero dead leg valve." Such a non-dead leg valve for preventing dead leg spaces in a container or tubing is a valve in which a volume of a non-circulating length of tubing or a volume of a container in which there is no movement of liquid is no greater than about one centimeter cubed (1 cm$^3$). Typically, a non-dead leg valve has a volume of non-circulating liquid from about 0.1 cubic centimeter (0.1 cm$^3$) to about one centimeter cubed (1 cm$^3$).

The term "about," as used herein refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by 1/10 of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

In one embodiment the non-dead leg valve assembly is flush-mounted, that is, even-mounted with the wall in which it is installed, such that the distance it protrudes into the container or tubing is substantially less than the distance a non-flush-mounted valve would protrude. The disclosed valve assembly includes an annular flange or fitting 22 having an inner edge 26 defining an opening 24 through which the perforated screen 38 at the bottom of the assembly is visible.

Figure 1B:
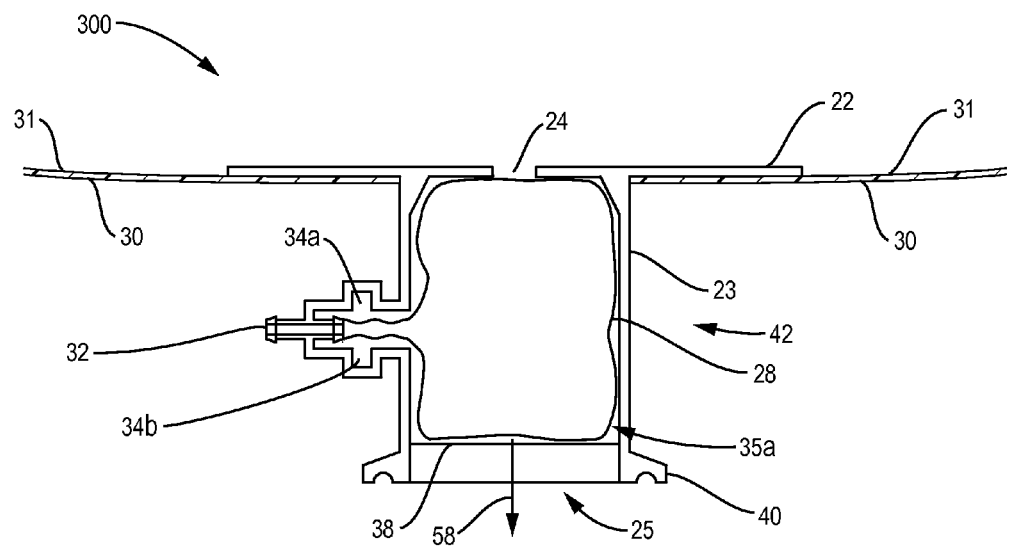
FIG. 1B is a sectional, side elevational view of a single-use flush mount, balloon seal valve according to an embodiment of the invention.

FIG. 1B is a side elevational, partial cutaway view 300 of the assembly shown in FIG. 1A. The valve assembly comprises: a bulkhead fitting 42 comprising an annular flange 22 for attaching the valve assembly to one surface of a flexible or semi-rigid wall of a container or tubing 31, such that an opening 24 in the center of the annular flange 22 is in communication with an aperture in the flexible or semi-rigid wall of the container or tubing 31; a hollowing housing 23 attached to the annular flange 22, the hollow housing 23 having a liquid inlet communicating with the opening 24 in the center of the annular flange 22, and a liquid outlet 25 at or below the perforated screen 38, the hollow housing 23 comprising a gas port 32, and an inflatable bellows or balloon 28 fluidically connected to the gas port 32.

The flange 22 is preferably welded to the inner surface 31 of bag film or tubing or welded to the outer surface 30 of the bag film or tubing, or attached via a mechanical or a magnetic coupling. If, as in FIG. 1B, the flange is welded to the inner surface 31 of bag film, e.g., it is referred to as a "bulkhead fitting." As used herein, the term "bulkhead fitting" means a fitting that attaches through a wall for allowing passage of, for example, a fluid, tubing, a sensor, and the like. In a bulkhead fitting, the container or tubing wall is often "sandwiched" between a plate or flange, e.g., and the body of a housing or a main portion of an assembly, wherein the bulkhead fitting is adapted for sealing against an aperture to provide a fluid-tight passageway. If the flange 22 were attached instead to an outer surface of the flexible or semi-rigid wall, it would not be a bulkhead fitting. Other types of bulkhead fittings are described in PCT/US2012/55081 filed 13 Sep. 2012, the teachings of which are incorporated herein by reference in their entireties.

In the embodiment shown in FIG. 1B, the annular flange 22 is integral with the hollow housing 23, such that opening 24 is the opening in both the hollow housing 23 and the flange 22. In another embodiment, not shown, the annular flange 23 may be sealingly attached to the hollow housing 23 such that the opening 24 in the annular flange 22 is adjacent and to and in fluid communication with an opening in the hollow housing 23.

FIG. 1B is a side elevational view of the inflated bellows style single use flush mount, non-dead leg valve 300. Within the hollow housing 23 is a bellows or balloon 28, preferably formed of silicone rubber, for example, or another suitable thin-walled thermoset or thermoplastic, elastic material. The bellows 28 is capable of expanding and contracting when pressure or a vacuum is applied to it, respectively. The bellows 28 will be sized such that when a larger pressure than the hydrostatic head and overhead pressure is applied to it, it will inflate, thereby blocking the upper opening 24 of the fitting 22 which is open to the internal and external surfaces of the bioreactor bag 31, 30. A filter may be positioned upstream of gas port 32. The sides of the hollow housing 23 will restrict the bellows 28 in the side direction. As shown in the figure, in one embodiment a perforated screen 38 on the bottom opening of the housing 23 functions to provide a support to keep the bellows 28 in place and from shifting under the pressure of the fluid behind the bioreactor bag surfaces 31, 30. The use of the perforated screen 38 is one potential configuration, depending on the application.

When the operator wishes to activate fluid flow through the valve 300, then s/he simply applies a vacuum through gas port 32 to the bellows 28 shown in an inflated condition 35a, and the bellows 28 will deflate and be drawn inside of the side port air supply cavity portion 34a, 34b within the hollow housing 23. The deflation of the bellows 28 opens up a pathway to fluid flow out of the bioreactor, through the hollow housing 23, through the perforated screen 38, and out of the liquid outlet 25 of the hollow housing 23 in the direction shown by arrow 58.

In addition to drawing a vacuum for deflation of the bellows 28, gas port 32 can also be used to inflate bellows 28. Cavity 34a, b forms a seal that prevents fluid flow in a lateral direction. Upon deflation, bellows 28 retracts into cavity 34a, b. Perforated screen 38 retains bellows 28 while allowing flow-through. Ferrule 40 is a connection to drain tubing (not shown).

Figure 2A:
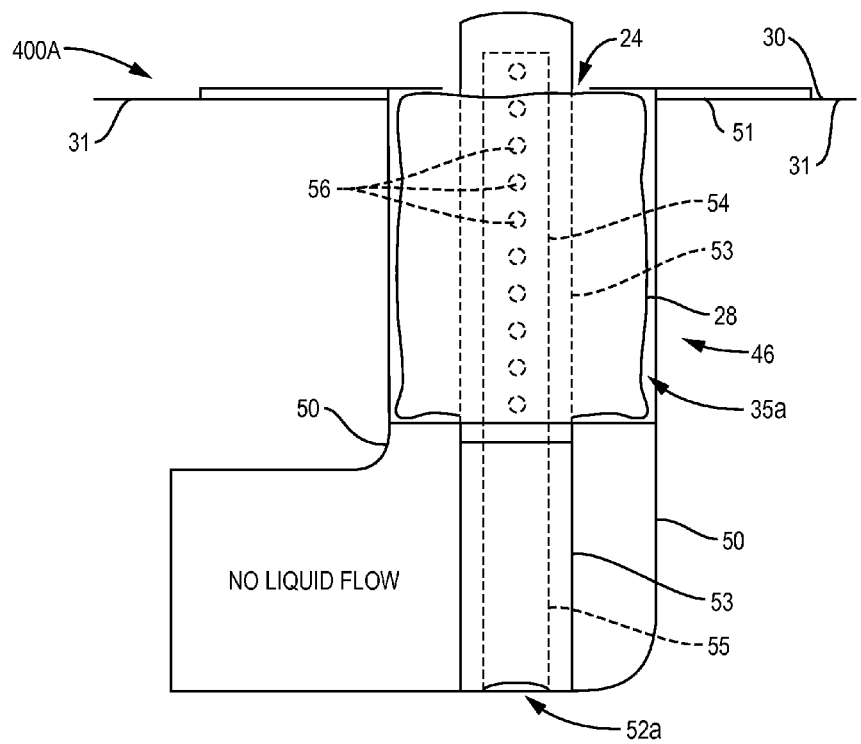
FIG. 2A is a side elevational view of an elbow-shaped balloon style single-use flush mount, balloon seal valve in closed position according to an embodiment of the invention.
Figure 2B:
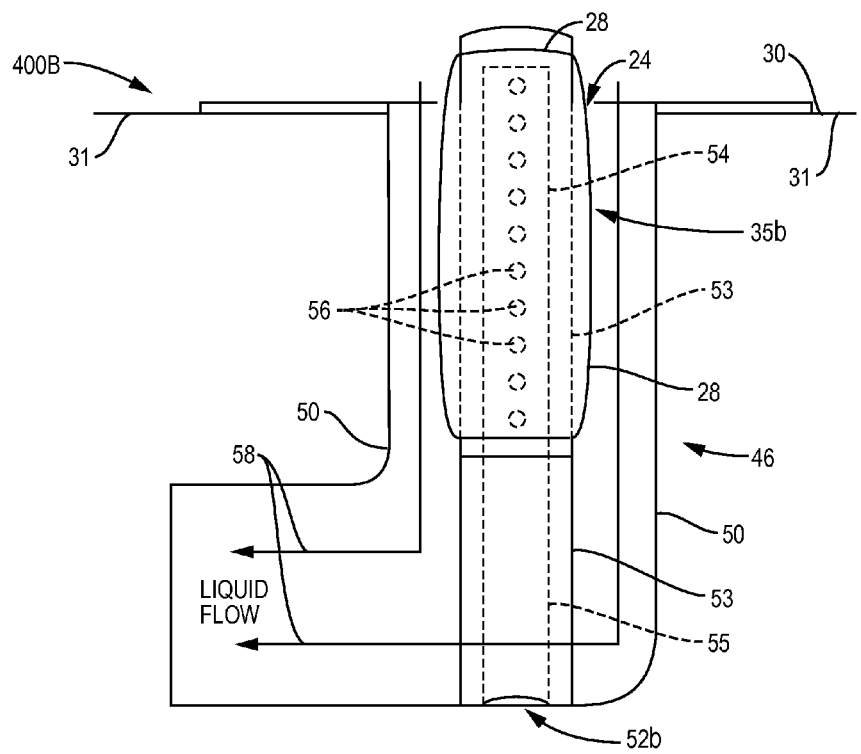
FIG. 2B is a side elevational view of an elbow-shaped balloon style single-use flush mount, balloon seal valve in open position according to an embodiment of the invention.

A second embodiment of a bulkhead fitting 46, shown in FIGS. 2A and 2B, is functionally similar to the above-described valve shown in FIGS. 1A and 1B. The bulkhead fitting 46 comprises a hollow housing 50 having an annular welding flange 51 welded or sealed to the inside flexible wall 30 of a bag or tubing. As shown in FIG. 2A, in place of a perforated screen, the bottom of the valve body, hollow housing 50, is elbow-shaped, and the right angle bottom portion of the valve supports the inflated bellows 35a. As shown in FIG. 2B, the annular flange 51 defines an opening 24, allowing the deflated bellows 35b to extend slightly into the bulk fluid within the bioreactor bag formed by the flexible wall having inner bag surface 30, and outer bag surface 31.

FIG. 2A and FIG. 2B show air port 52a, 52b, respectively, as an entrance to the inflation tube stem 55 attached to the bottom end of balloon inflation tube 54. Inflation tube 54 includes inflation ports 56 and is axially disposed within balloon support tube 53.

FIG. 2A depicts the balloon seal valve 400A in a closed position, with gas pressure applied. The main sealing surface in this configuration is between the bellows 28 and the inside vertical side wall of the annular welding flange 28. When the balloon is inflated 35a there is no liquid flow through the hollow housing 50. FIG. 2B depicts the balloon seal valve 400B of FIG. 2A in an open position with no gas pressure applied, and a deflated balloon 35b. Liquid can flow from the flexible bioreactor or mixer bag or the tubing through opening 24 and through the hollow housing 50 in the direction shown by arrows 58.

Figure 3A:
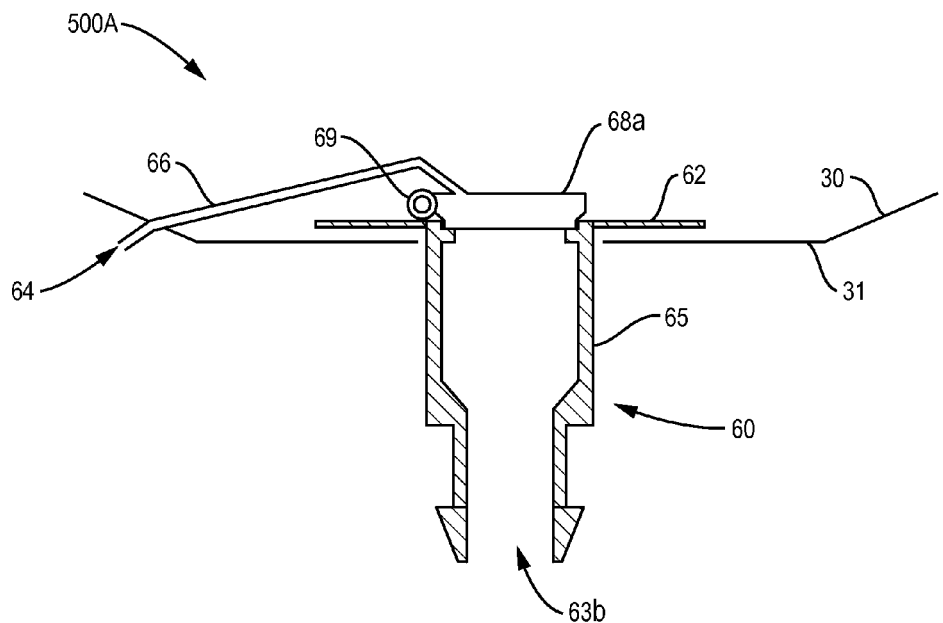
FIG. 3A is a cross sectional side elevational view of the buoyant flap style single-use flush mount valve, in a closed position according to an embodiment of the invention.
Figure 3B:
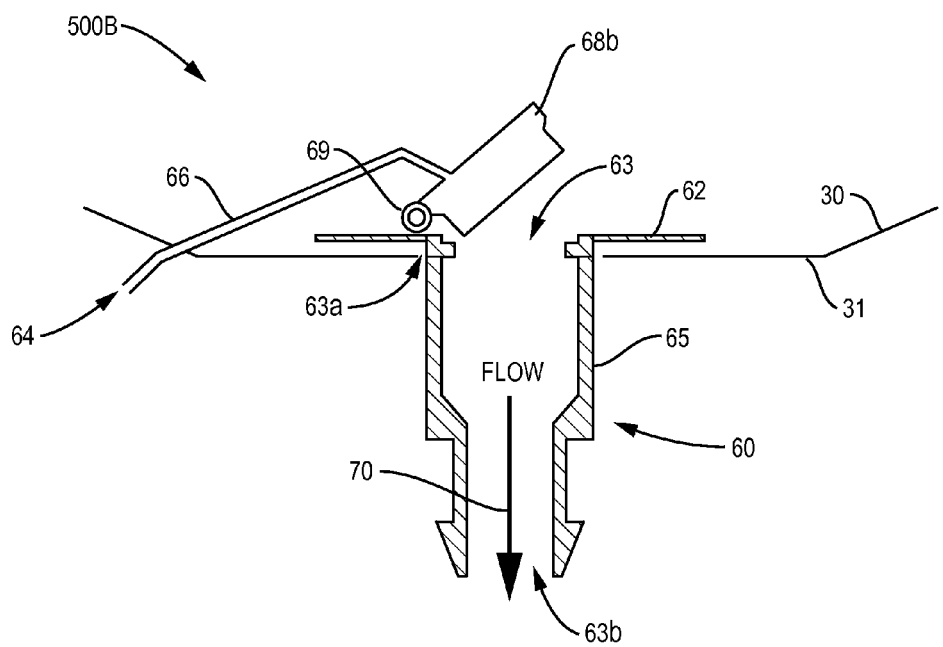
FIG. 3B is a cross sectional side elevational view of the buoyant flap style single-use flush mount valve, in an open position according to an embodiment of the invention.

A third embodiment as shown in FIGS. 3A and 3B are each a cross sectional side elevational view of the buoyant flap style single-use flush mount valve, in a closed position and an open position, 500A, 500B, respectively.

The embodiment shown in FIGS. 3A and 3B is a valve assembly for preventing dead leg spaces in a container or tubing, the valve assembly comprising: a first component comprising a bulkhead fitting 60 for attaching the valve assembly to the inside of a flexible or semi-rigid wall 30 of the container or tubing, the bulkhead fitting 60 comprising an annular flange 62 for mounting and sealing the fitting 60 on the inside of the flexible or semi-rigid wall 30 of the container or tubing such that an opening 63 in the center of the annular flange 62 is in communication with an aperture 63a in the flexible or semi-rigid wall of the container or tubing; a hollow housing or valve body 65 attached to or integral with the annular flange 62 of the bulkhead fitting 60, the hollow housing 65 comprising: a liquid inlet 63 communicating with the opening 63 in the center of the annular flange 62 and configured for receiving a liquid from the container or tubing; a liquid outlet 63b; and a second component comprising a hollow tubing 66 having a first end mounted at the flexible or semi-rigid wall 30, 31 of the container or tubing, the first end of the hollow tubing communicating with a gas port 64 in the flexible or semi-rigid wall of the container or tubing, the second end of the hollow tubing having an inflatable and deflatable hollow member 68a, 68b in fluidic communication with the hollow tubing 66 and sized to seal the opening 63 in the center of the annular flange 62; the inflatable and deflatable hollow member 68a, 68b comprising a hinged portion 69 attached to the annular flange 62 and supporting the hollow member 68a, 68b for reciprocating movement between a lower position (FIG. 3A) where the hollow member 68a is compressed by a hydrostatic pressure of fluid in the container or tubing and seals the opening 63 in the center of the annular flange 62, preventing fluid from entering the hollow housing 65 and an upper position (FIG. 3B) spaced from the lower position, the upper position providing an opening for fluid flow in the direction shown by arrow 70 through the opening 63 in the center of the annular flange 62; and a means coupled to the second component and extending outside the container or tubing for selectively moving the hollow member 68a, 68b between the upper and the lower positions.

In one embodiment of the disclosed valve assembly 500A, 500B, the means for selectively moving the hollow member between the upper and the lower positions comprises a gas flow through the gas port 64, into the hollow tubing 66, and into the hollow member 68a, 68b, wherein the hollow member is inflated 68b with sufficient gas pressure to move the hollow member from the lower position FIG. 3A to the upper position FIG. 3B.

The hollow member 68 a,b may be formed from as an elastomeric or rubber hollow body that is inside the bag 30, but connected to the outer circumference of the flange 62 by a hinge 69. The stem portion of the valve body 65 provides the entry or exit point for tubing with the bioreactor. The hollow member is sized so that it fits over the opening 63 of the flange 62 and is compressed by the hydrostatic pressure of the fluid, thereby providing a seal and preventing fluid from entering the housing 65. The hinge 69 at one end of the hollow member 68 a, b provides a pivot point for the member 68a, b to be swung open or closed. When the operator wishes to activate fluid flow through the valve, then the hollow member can be pushed upwards by inflating the top of the hollow member with air. The buoyancy of the air will lift the hollow member upwards, providing an opening 63 for fluid flow into the hollow housing 65 and out the opening 63b.

Figure 4A:
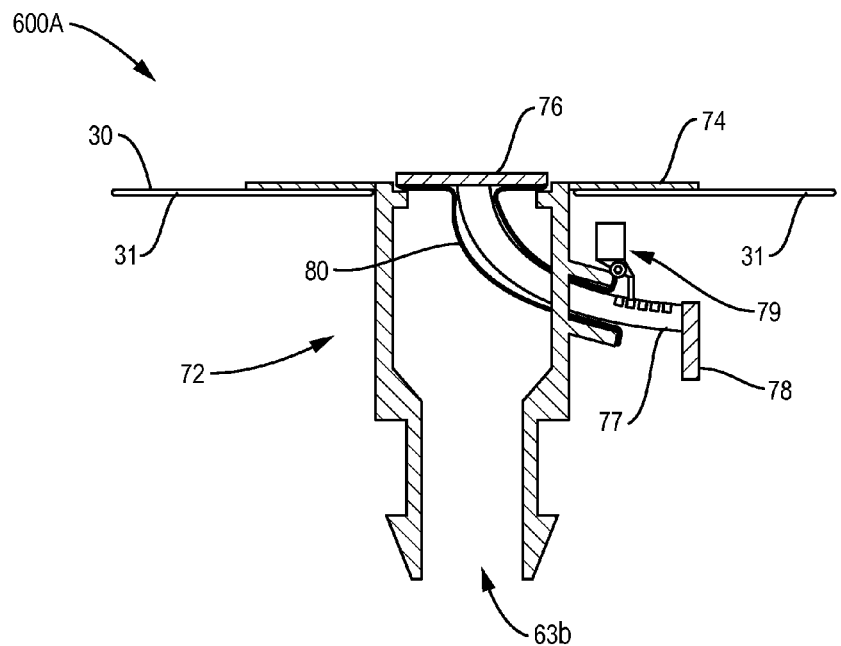
FIG. 4A and FIG. 4B are each a cross sectional side elevational view of the ratchet style single-use flush mount valve, in a closed position and an open position, respectively according to an embodiment of the invention.
Figure 4B:
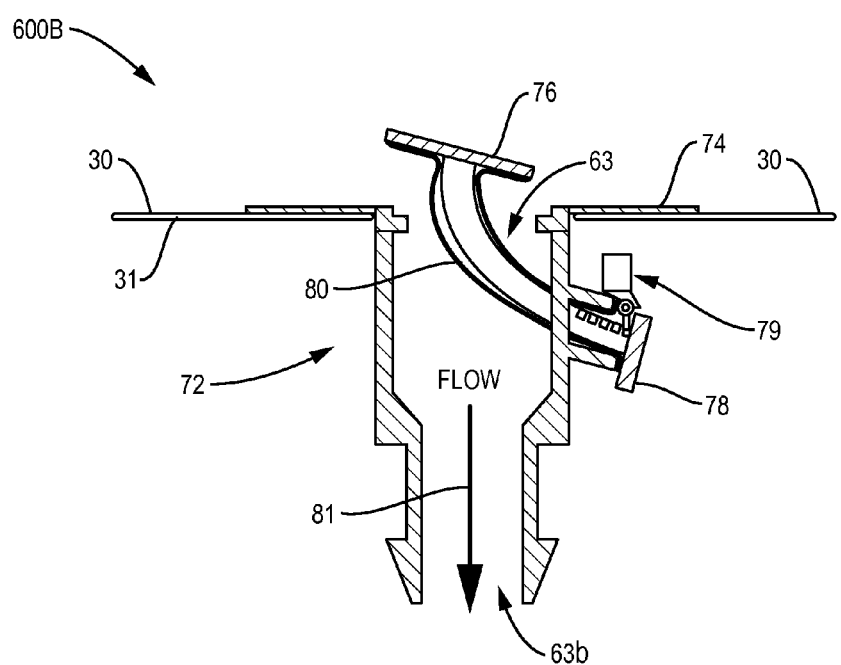

A fourth embodiment is shown in FIG. 4A and FIG. 4B, which are each a cross sectional side elevational view of the ratchet style single use flush mount valve, in a closed position 600A and an open position 600B, respectively. The ratchet style valve is functionally similar to the third embodiment. However in the ratchet style valve, a sealing flap 76 corresponding to hollow member 68a,68b is either attached to or integral with a curved rod or valve stem 77 and can be pushed open, e.g., at thumb pad 78 from the side of the hollow housing or valve body 72. A ratchet mechanism 79 secures the position of the sealing flap 76 with respect to the valve opening and can thus be opened to varying amounts. The ratchet mechanism 79 provides discrete values for which the valve can open, thus providing a varying of set values for flow rates. The rates can be pre-determined, e.g., based on the sizing of the system and the supply pressure.

The sealing flap 76 can be moved between a closed position 600A shown in FIG. 4A, and an open position 600B shown in FIG. 4B, allowing fluid to flow from a container, e.g., through opening 63 in the valve body 72 and out of the valve body 72 through opening 63b in the direction shown by arrow 81.

In one embodiment, at least a portion of the valve stem 77 and the sealing flap 76 are covered with an elastomeric material, e.g., a bellows 80 that provides an improved seal to isolate the valve stem 77 from the bag or tubing contents.

Figure 5A:
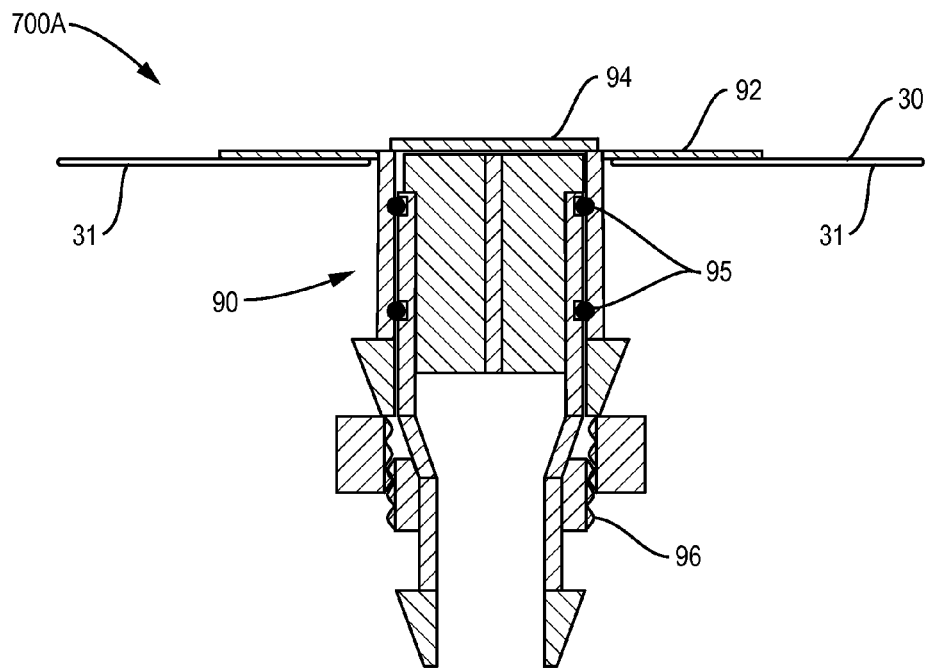
FIG. 5A and FIG. 5B are each a cross sectional side elevational view of a plunger style single-use flush mount valve in a closed position and an open position, respectively according to an embodiment of the invention.
Figure 5B:
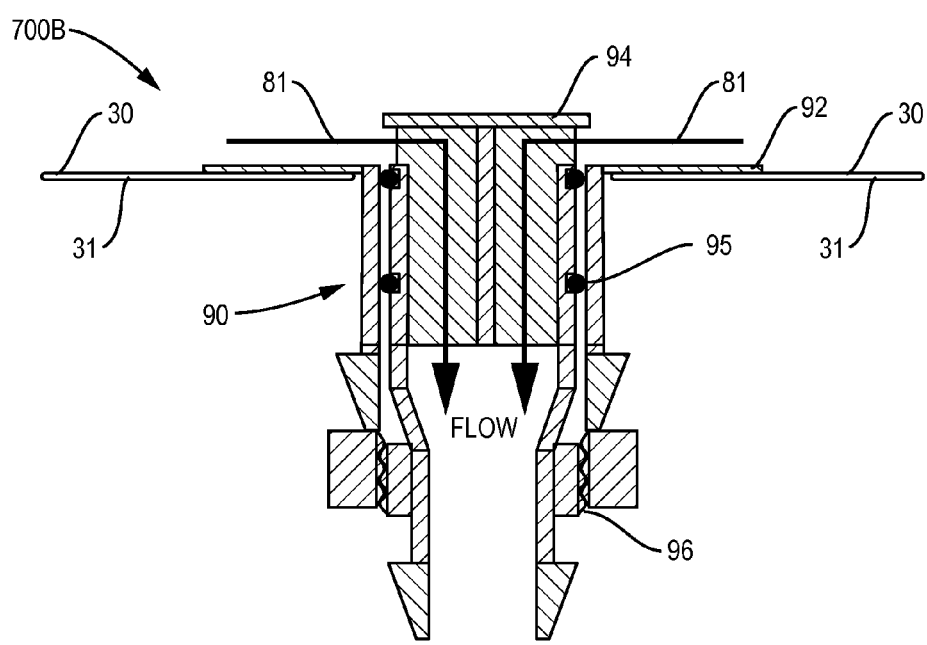

A fifth embodiment of the invention is shown in FIGS. 5A and 5B, which are each a cross sectional side elevational view of a plunger style single-use flush mount valve in a closed position (FIG. 5A) and an open position (FIG. 5B). The plunger style valve is functionally similar to the fourth embodiment. The plunger style valve comprises a plunger 94 that is actuated in the linear direction of flow shown by arrows 81 through the hollow housing or valve body 90. The valve body 90 is attached to or integral with an annular flange 92 that seals the valve body 90 to the inside surface of the flexible wall 30. In one embodiment, the plunger 94 is raised by a threaded or screw type mechanism 96, allowing flow between the plunger 94 and the valve body 90. The outer edge of the plunger 94 inside the valve is sealed via o-rings 95, gasket or other elastomer. This seal ensures flow is directed around the plunger and maintains a sterile barrier between the internal system and the external environment.

Figure 6:
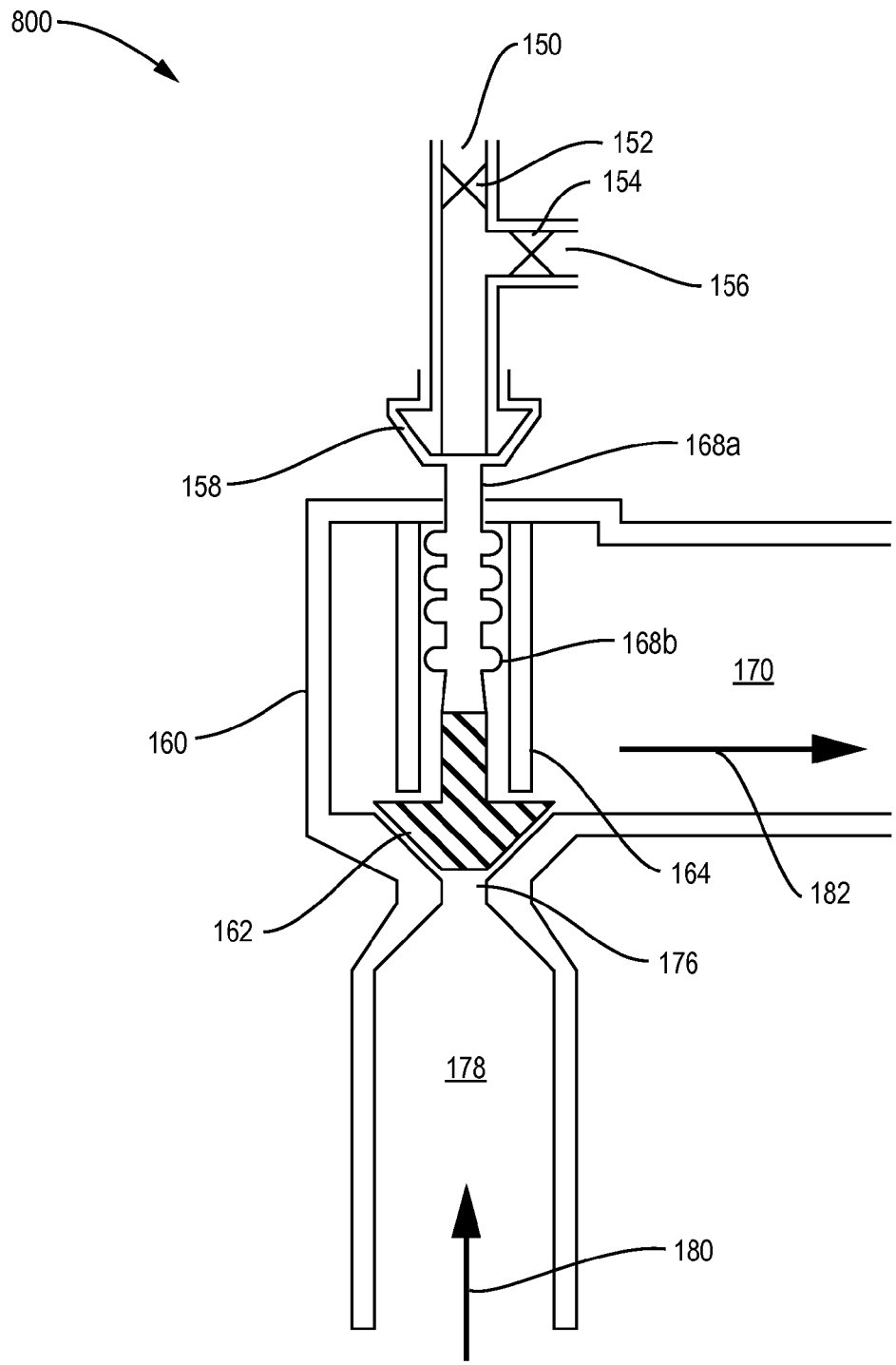
FIG. 6 is cross sectional side elevational view of an orifice plunger style single-use pressure control valve or poppet valve according to an embodiment of the invention.

A sixth embodiment, as shown in FIG. 6, is cross sectional side elevational view of an orifice plunger style single use pressure control valve 800. The orifice plunger valve 800 can be used to control or regulate the flow across a range of values.

The embodiment shown in FIG. 6 is a three-way valve assembly 800 for controlling back-pressure in a fluid generating device, for example, a bioreactor or a mixer. The three-way valve assembly comprises: a main valve body portion 160 adapted at one end to engage an inlet 178 for exhaust fluid flowing in the direction shown by arrow 180 from the fluid generating device, the main valve body portion 160 defining a central axis; a valve stem 168a or bellows 168b having a first end and a second end, comprising a solid plunger 162 at the first end and disposed axially within the main valve body portion 160, the bellows 168b or valve stem 168a supported for reciprocating axial movement between a first position wherein the solid plunger 162 closes the orifice 176 of the inlet 178 for exhaust fluid from the fluid generating device and a second position wherein the solid plunger 162 opens orifice 176 of the inlet 178 for exhaust fluid from the fluid generating device; and a two-way valve 150 coupled to the second end of the bellows 168b or valve stem 168a, the two-way valve 150 configured to selectively control a gas inlet 152 for inflating the bellows 168b and a gas outlet 154 for deflating the bellows 168b. The solid plunger 162 may be rigid and shaped, for example, tapered, to better seal orifice 176.

The three-way valve assembly 800 may thus be configured in a manner to move the bellows 168b to the first position wherein the solid plunger 162 closes the orifice 176 of inlet 178 for exhaust fluid when the bellows 168b are inflated, and to move the bellows 168b to the second position wherein the plunger 162 opens the orifice 176 of inlet 178 for exhaust fluid when the bellows 168b are deflated.

With no more than routine experimentation, the valve stem 168a or bellows 168b could be replaced by a spring or other tension creating device that can be compressed downward to push solid plunger 162 downward to close the orifice 176 of the inlet 178 for exhaust fluid from the fluid generating device; and when decompressed, allow solid plunger 162 to move upward to open the orifice 176.

In one embodiment, a gas such as air is supplied into a bellows 168b formed of rubber or other elastomeric material, and the bellows 168b is contained by a sidewall or open tube 164. The sidewall or tube 164 prevents the bellows 168b from expanding outwards on its side and instead restricts motion to an axial direction. The bellows 168b can be pressurized and depressurized with a gas.

In the orifice plunger style valve, 152 is the air inlet valve for inflating the bellows 168b. Vent 156 allows for deflating bellows 168b, with valve 154 arranged in the vent outlet 156. 158 is a three-way valve and bellows assembly which will be permanently attached to the main valve body. 60 is the main valve body 160. 162 is a solid plunger for controlling pressure through the orifice 176. 164 is a tube for retaining the bellows 168b and directing motion axially. 170 is the process exhaust gas outlet which allows exhaust gas to move out of the system in the direction indicated by arrow 182 when plunger 162 moves upward to open orifice 176.

Use of the three-way valve assembly 800 in a high pressure microbial bioreactor is effective in increasing backpressure in order to increase dissolved oxygen concentration. Maintaining high oxygen concentration is critical for meeting the oxygen demand of a microbial culture. In general, disposable or single-use bioreactor bags have limited ability to withstand extremely high pressure, so controlling the backpressure is especially important in microbial cultures carried out in single-use, flexible bags.

Figure 7A:
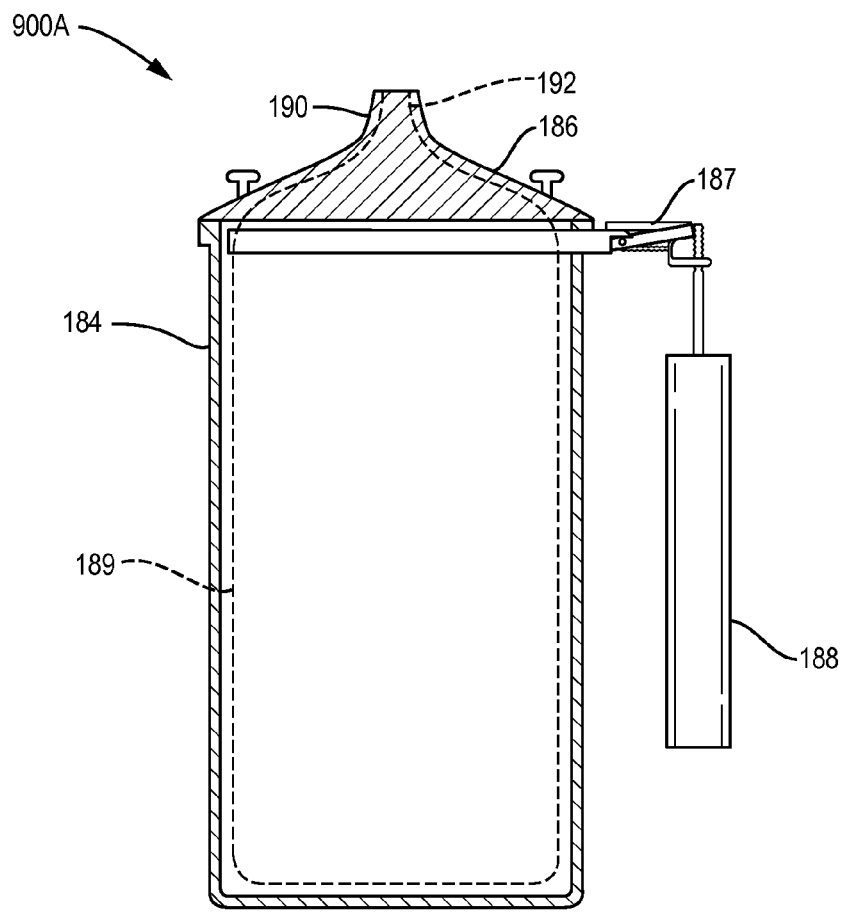
FIG. 7A is a schematic, cross-sectional view of a pressurizable reactor system according to the invention with a flexible or disposable reactant container.

In yet another aspect of the invention, pressurizable flexible liners for pressurizable single-use vessels are also disclosed. Turning now to FIG. 7A, a disclosed pressurized reactor system 900A for use in biomanufacturing is shown. The pressurized reactor system ("PRS") combines a flexible liner and support structures of various configurations. The PRS is pressurizable but is also easy to load and unload. In one aspect, nearly fully closed pressurizable support structures with easy open/close features are disclosed.

One embodiment of the invention comprises a PRS support structure including a nearly fully closed outer vessel 184 that contains a flexible bioprocessing bag liner 189. The support vessel 184 has relatively small vessel ports which mate to matching pressure fittings on the flexible bag liner 189 that is placed inside the vessel 184. By proper combination and alignment of the flexible liner port fittings with the mating vessel ports, the system can be pressurized. The outer vessel support structure 184 can be constructed to open quickly and ergonomically with counter-weighted assist devices 188, 187 that improve the ergonomics of loading and unloading the flexible container 189.

Figure 9:
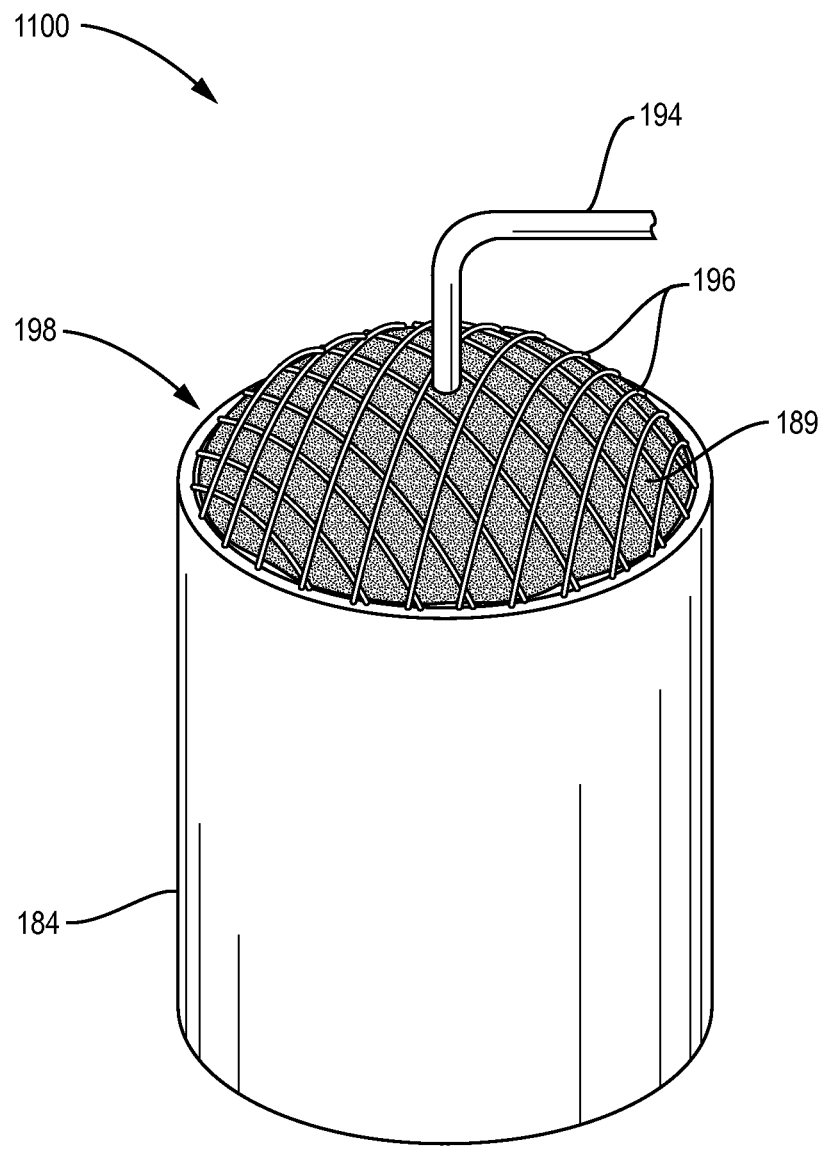
FIG. 9 is schematic, perspective view of an alternative pressurizable reactor system according to the invention in which the flexible or disposable reactant container is retained within a support structure by a retaining element.

FIG. 9 depicts another embodiment of a PRS 1100 that includes a partially open support structure 184 having opening 198 and employs a retaining net 196, screens or webbing to support and/or stabilize a flexible or disposable reactant container 189. In this embodiment the support structure can a partially open support structure 184 containing the liner or disposable container 189, and the liner/container 189 is retained in the vessel 184 during pressurization by retaining net material 196 that is fastened to the support structure/ vessel 184 and which spans the large openings 198 of the support structure 184. The openings in the netting 196 receive and retain the pressure fittings of the pressurizable liner 189. Loading and unloading the flexible liner 189 from the system is facilitated by the flexible webbing/netting 196 that can be quickly disconnected from the support structure 184 to clear the way for bag 189 removal.

The flexible liner 189 may also be reinforced as described below to withstand elevated pressures and temperatures. In certain embodiments, the flexible liner is designed to withstand significant pressures via the use of pressure fittings and/or reinforcing components, fibers or layers as part of the wall of the flexible liner, or combinations of both pressure fittings and reinforced materials.

The pressure fittings of the present invention can include machined or molded plastic elements attached to a flexible liner (with or without liner reinforcing components) such that in combination the fitting elements combine to form a pressurizable liner that can withstand high pressures. When pressure is applied to the flexible liner within the pressure vessel, the pressure within the container forces the pressure fitting into a corresponding shaped fitting on the pressure vessel, thereby forming a fully supported pressure-tight seal of the single use container within the vessel. The system may then be pressurized well above the normal burst pressure limit of a single-use container to allow higher levels of dissolved gasses, e.g., dissolved oxygen in a cell culture or high pressure transfer of material from the single-use container to another system. Single-use pressure fittings may be used to add liquids or gases into a single-use container inside a pressure vessel and allow the penetration of sensors while maintaining high pressure within the flexible container.

Figure 7B:
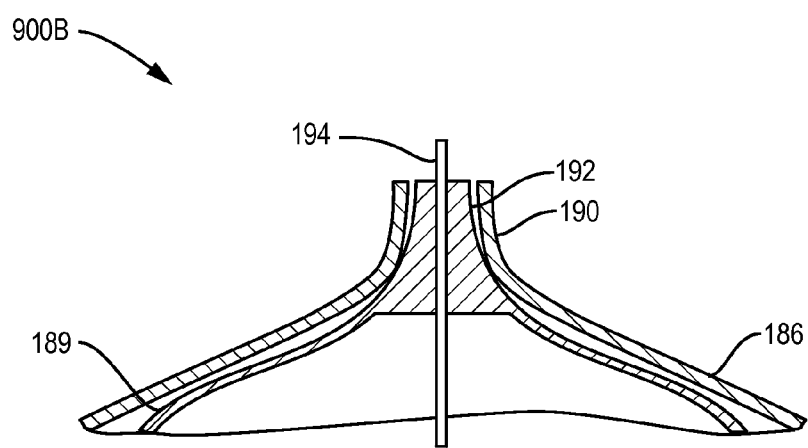
FIG. 7B is an enlarged, cross-sectional view of a port or fitting component of the system of FIG. 7.
Figure 8:
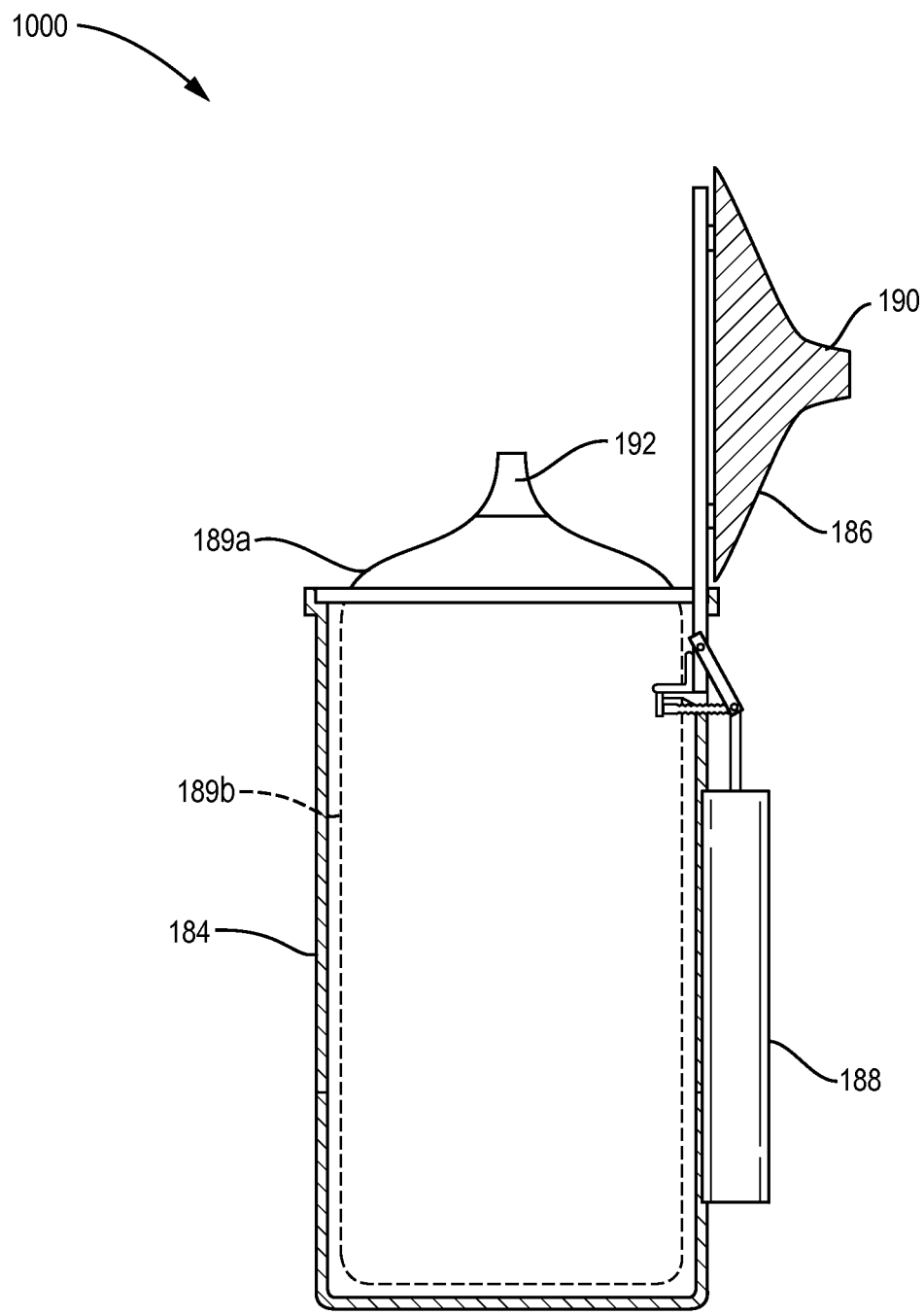
FIG. 8 is schematic, cross-sectional view of the pressurizable reactor system of FIG. 7A-7B where the support structure is in an open position with a flexible or disposable reactant container therein.

FIGS. 7A, 7B and 8 illustrate one embodiment of the invention in which a pressurized reactor system, PRS, 900A is shown. FIG. 7A shows a PRS 900A having an outer support structure that includes a body 184 and top 186, including port fitting 190. The port fitting 192 on top of flexible container 189 is shown to conform and fit within the port fitting 190. Hinge 187 is configured to open the top 186 with assistance of counterweight 188. As shown in FIG. 8, PRS 1000 has a top 186 that can be opened with the assistance of counterweight 188. Within the support structure body 184 is a high performance flexible container or liner 189b, 189a having one or more port fittings 192. As shown in more detail in FIG. 7B, a cross sectional elevational view 900B shows that port fitting 192 can be configured to mate with a corresponding fitting port 190 on top 186. Also depicted is tubing 194 that is a fluidic connection to the interior of the flexible bag.

FIG. 9 illustrates another embodiment of a PRS 1100 in which partially open support structures 184 with fluidic connection via tubing 194 to interior of flexible bag 189 are disclosed. Flexible bag 189 has a retaining element 196, e.g., a net, screens or webbing to support and/or stabilize a flexible or disposable reactant container 189. In this embodiment the support structure can be a partially open support structure 184 containing the liner or disposable container 189, and the liner/container is retained in the vessel 184 during pressurization by retaining net material that is fastened to the support structure 184 and which spans the large openings 198 of the support structure. The openings in the netting receive and retain the pressure fittings 26 of the pressurizable liner. Tubing 194 can pass through the port fittings 192, 190 to deliver or remove gases or fluids, e.g., nutrients or reactants, or to permit monitoring of the processes, e.g., with sensors. Loading and unloading the flexible liner from the system is facilitated by the flexible webbing/netting 196 that can be quickly disconnected from the support structure 184 to clear the way for bag removal. The flexible liner 189 may be reinforced to withstand elevated pressures and temperatures.

Assembly variations are shown in FIGS. 10A-18B. The assemblies can include a molded or machined plastic plug 201. The plug 201 may be a straight (FIG. 10 or 12) or tapered (FIG. 11 or 13), square, ball, hemispherical, or cylindrical plastic shape. The plug 201 can be removable or mounted permanently to a plastic flexible or semi-rigid container or bag 189 and the plug 201 fits into a corresponding shaped vessel fitting, adapter, or insert 203 on the wall of a pressure vessel 204 from the inside of the vessel 204. To seal the plug 201 within the pressure vessel 204 and corresponding vessel fitting, the plug 201 can utilize a single gasket 205 or O-ring 206 or series of sealing components. The plug can incorporate a small raised portion of plastic material emanating from the body of the plug as a sealing component (Figure variation 10B, 11B), or the pressure inside the vessel and the shape of the plug and fitting may act to provide a pressure tight seal of the pressure vessel. Handles or other protruding devices 207 can be attached to the plug in order to manipulate it into position.

Figure 14:
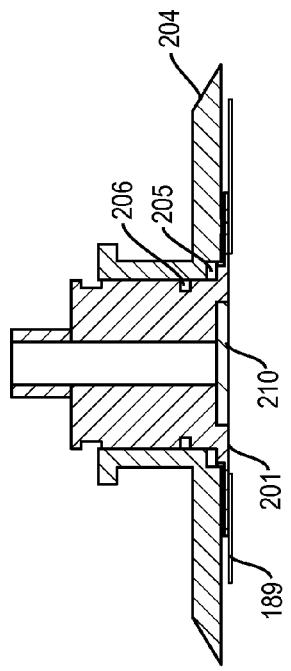
FIG. 14 is a schematic, cross-sectional view of one embodiment of a pressure fitting for sensors according to the invention.
Figure 15:
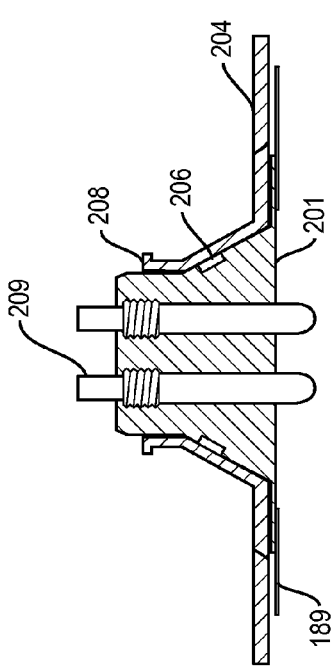
FIG. 15 is a schematic, cross-sectional view of one embodiment of a pressure fitting for a gas sparger according to the invention.

In order to transfer material from inside to the outside of the pressure vessel/flexible container system each plug 201 may incorporate a single or series of penetrations 208. As shown in FIG. 14, plugs 201 may also act as mounts for incorporation of a sensor or many sensors 209 into the pressure vessel/flexible container system (FIG. 14). Gases may be introduced through a perforated disc or filter material 210 into the flexible container at high pressure thru the pressure vessel fitting (FIG. 15).

Figure 16:
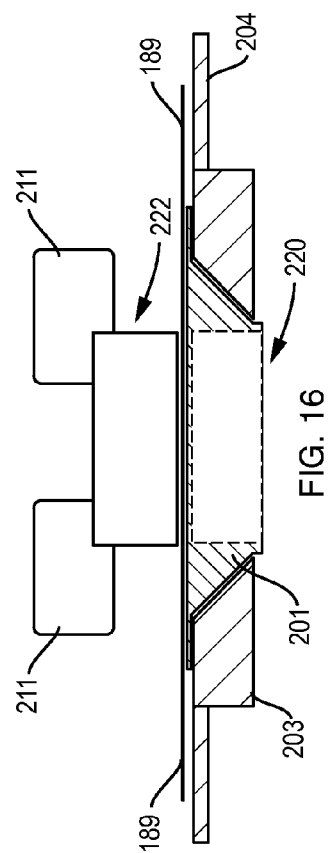
FIG. 16 is a schematic, cross-sectional view of one embodiment of a pressure fitting for an impeller assembly according to the invention.

As depicted in FIG. 16, other uses of the pressure vessel fitting may be to provide support for magnetically coupled devices such as agitators or impellers 211 having a magnetic hub 222. A magnetic drive 220 is positioned external to the bag 189. The wall 204 of the pressure vessel is shown, with an insert of a molded or machined plug 201 and a correspondingly shaped vessel fitting or adapter 203, the insert plug 201 and adapter 203 adding support to a pressurized flexible bag 189.

FIGS. 17A-17B and 18A-18B illustrate another aspect of the invention, in which reinforced flexible liners 212A, 212B, 212C, and 212D respectively, reinforced with components, fibers 214A, 214B, 214C, 212D or layers, can form all or part of the wall of the flexible liner 189. In the illustrated embodiments, the film 212A, 212B, 212C, 212D that comprises the single use container for bioprocessing contains reinforced fibers 214A, 214B, 214C, and 214D, respectively, inside the film capable of withstanding pressures of 1 bar or more. One embodiment has a thermoplastic layer formed of a material such as polyethylene, which is compatible with standard industry fittings, a second layer of fibrous or woven high tensile strength material in a cross-hatching or other type of reinforcing pattern (such as nylon or even silicone encapsulated stainless steel), and a third layer of thermoplastic material with one side of the third layer potentially the same material as the first layer. The third layer can be a single polymer film or multiple polymer coextruded or cast film that has other desirable properties, such as reduced gas and/or water vapor transmission and increased tensile strength as examples. The inner side of the third layer is ideally but not limited to the same material as the first layer to help facilitate bonding of the first and third layer, which sandwiches the reinforcing second layer.

Figure 17A:
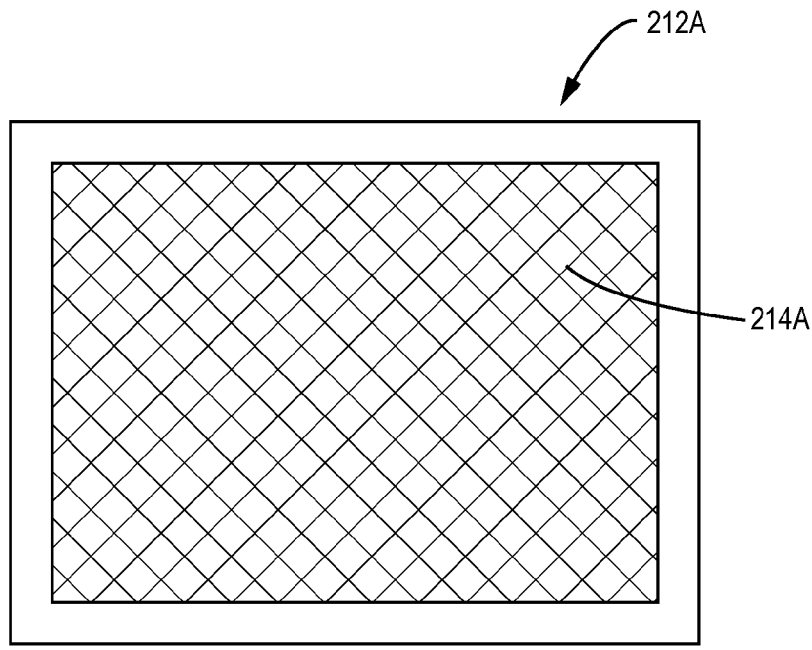
FIG. 17A is a schematic, top view of one embodiment of a reinforcing construct according to the invention.
Figure 17B:
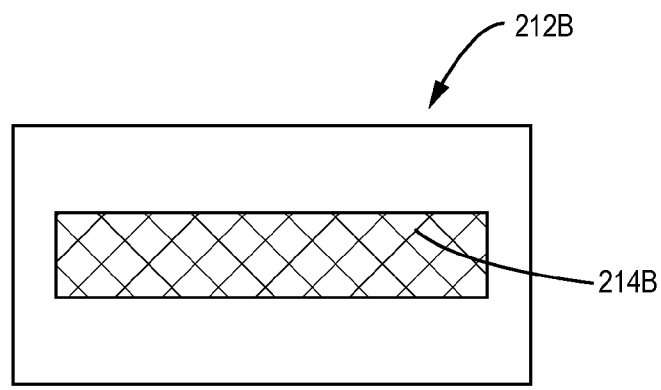
FIG. 17B is a schematic side view of the construct of FIG. 17A.

The size of the reinforcement second layer can be controlled during the manufacturing of the film such that the edges of the film only comprise the first and third layers. This type of orientation makes the cutting and welding of the film easier to fabricate into objects that can be formed or sealed together and hold pressure. This is of use in fabricating single use liners in the bioprocessing industry. FIGS. 17A-17B provide an example of this type of film.

Figure 18A:
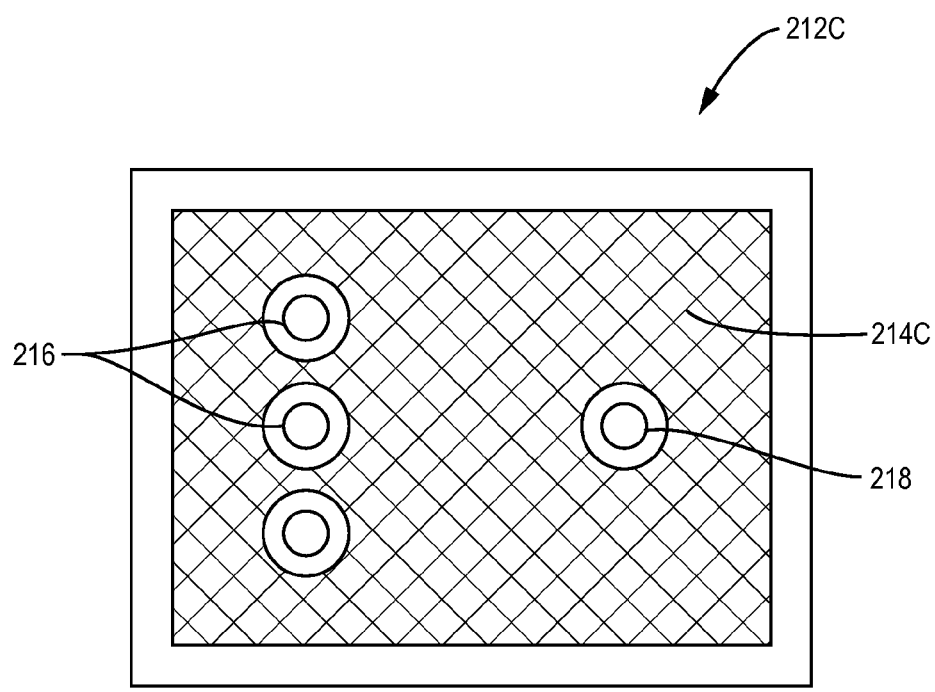
FIG. 18A is a schematic, top view of one embodiment of a reinforcing construct and incorporated fittings according to the invention.
Figure 18B:
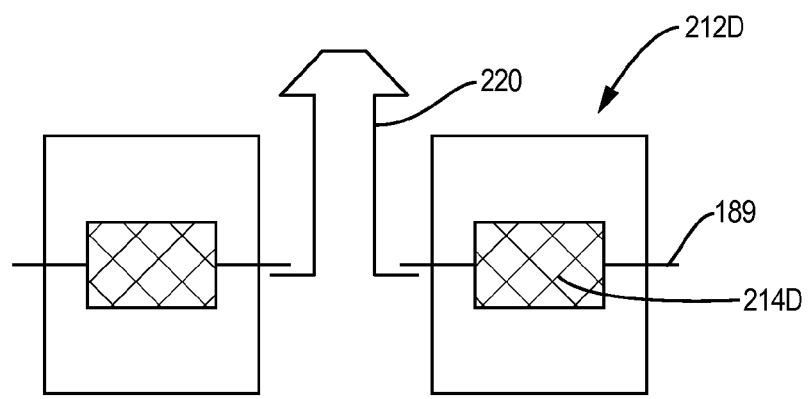
FIG. 18B is a schematic side view of the construct of FIG. 18A.

FIG. 18A shows another embodiment of the film 212C cast with holes 216, 218 already in place to weld fitments for fluid transmission in and out of the finished object, such as a single-use liner for bioprocessing. FIG. 18B shows an embodiment of the film 212D with tubing port 220 in a reinforced film wall 189.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The invention claimed is:

1. A valve assembly for preventing dead leg spaces in a container or tubing, the valve assembly comprising:
   a bulkhead fitting for attaching the valve assembly to a flexible or semi-rigid wall of the container or tubing, the bulkhead fitting comprising an annular flange for mounting on one side of the flexible or semi-rigid wall of the container or tubing such that an opening in the center of the annular flange is in communication with an aperture in the flexible or semi-rigid wall of the container or tubing;
   a hollow housing attached to or integral with the annular flange of the bulkhead fitting, the hollow housing comprising:
      a liquid inlet communicating with the opening in the center of the annular flange and configured for receiving a liquid from the container or tubing;
      a liquid outlet;
      a gas port configured to be attached to a gas passageway and valve, wherein the valve is configured to selectively allow gas flow into the gas port or out of the gas port; and
      an inflatable and deflatable bellows or balloon fluidically connected to the gas port, and configured in a manner to inflate when gas flows into the gas port and into the inflatable bellows or balloon, thereby blocking the opening in the center of the annular flange and the aperture in the flexible or semi-rigid wall of the container or tubing, and to deflate when a vacuum is applied to the gas port, causing gas to flow out of the gas port and out of the bellows or balloon, thereby allowing liquid to flow out of the container or tubing, through the aperture in the flexible or semi-rigid wall of the container or tubing, through the hollow housing, and out of the liquid outlet of the hollow housing, the valve assembly thereby capable of preventing dead leg spaces in the container or tubing.

2. The valve assembly of claim 1, wherein the container or tubing comprises a single-use bioreactor system.

3. The valve assembly of claim 1, wherein the volume of a non-circulating or non-moving liquid is from about 0.1 cubic centimeter (0.1 $cm^3$) to about one centimeter cubed (1 $cm^3$).

4. A valve assembly for preventing dead leg spaces in a container or tubing, the valve assembly comprising:
   a first component comprising a bulkhead fitting for attaching the valve assembly to the inside of a flexible or semi-rigid wall of the container or tubing, the bulkhead fitting comprising an annular flange for mounting on the inside of the flexible or semi-rigid wall of the container or tubing such that an opening in the center of the annular flange is in communication with an aperture in the flexible or semi-rigid wall of the container or tubing;
   a hollow housing attached to or integral with the annular flange of the bulkhead fitting, the hollow housing comprising:
      a liquid inlet communicating with the opening in the center of the annular flange and configured for receiving a liquid from the container or tubing;
      a liquid outlet; and
      a second component comprising a hollow tubing having a first end mounted at the flexible or semi-rigid wall of the container or tubing, the first end of the hollow tubing communicating with a gas port in the flexible or semi-rigid wall of the container or tubing, the second end of the hollow tubing having an inflatable and deflatable hollow member in fluidic communication with the hollow tubing and sized to seal the opening in the center of the annular flange;
   the inflatable and deflatable hollow member comprising a hinged portion attached to the annular flange and supporting the hollow member for reciprocating movement between a lower position where the hollow member is compressed by a hydrostatic pressure of fluid in the container or tubing and seals the opening in the center of the annular flange, preventing fluid from entering the hollow housing and an upper position spaced from the lower position, the upper position providing an opening for fluid flow through the opening in the center of the annular flange; and
   a means coupled to the second component and extending outside the container or tubing for selectively moving the hollow member between the upper and the lower positions.

5. The valve assembly of claim 4, wherein the means for selectively moving the hollow member between the upper and the lower positions comprises a gas flow through the gas port, into the hollow tubing, and into the hollow member, wherein the hollow member is inflated with sufficient gas pressure to move the hollow member from the lower position to the upper position.

* * * * *